(12) United States Patent
Liu et al.

(10) Patent No.: US 11,982,649 B1
(45) Date of Patent: May 14, 2024

(54) SHEAR TESTING SYSTEM OF THERMO-SEEPAGE-MECHANICAL FIELD AND ENGINEERING DISTURBANCE COUPLING UNDER DEEP AND COMPLEX CONDITION

(71) Applicant: SICHUAN UNIVERSITY, Chengdu (CN)

(72) Inventors: Jianfeng Liu, Chengdu (CN); Heping Xie, Chengdu (CN); Chao Ma, Chengdu (CN); Fujun Xue, Chengdu (CN); Jingjing Dai, Chengdu (CN); Jianxiong Yang, Chengdu (CN); Lu Wang, Chengdu (CN); Zhijun Wu, Chengdu (CN); Xiangchao Shi, Chengdu (CN); Houquan Zhang, Chengdu (CN); Yinghui Ma, Chengdu (CN); Tao Meng, Chengdu (CN); Defu Zhu, Chengdu (CN); Shaoqi Kong, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/413,048

(22) Filed: Jan. 16, 2024

(30) Foreign Application Priority Data

Aug. 10, 2023 (CN) .......................... 202311000134.9

(51) Int. Cl.
*G01N 3/24* (2006.01)
*G01N 3/04* (2006.01)
(Continued)

(52) U.S. Cl.
CPC ................. *G01N 3/24* (2013.01); *G01N 3/04* (2013.01); *G01N 3/16* (2013.01); *G01N 33/24* (2013.01);
(Continued)

(58) Field of Classification Search
CPC .. G01N 3/24; G01N 3/04; G01N 3/16; G01N 33/24; G01N 2203/0025;
(Continued)

(56) References Cited

U.S. PATENT DOCUMENTS 5,105,687 A 4/1992 Paech
6,041,661 A 3/2000 McKinlay
(Continued)

FOREIGN PATENT DOCUMENTS

CN 104863569 A 8/2015
CN 206710188 U 12/2017
(Continued)

OTHER PUBLICATIONS

Haiyan Peng, Torsional vibration analysis of high power diesel engine high elastic coupling in fracturing truck and optimization, Sichuan University Master of Engineering Professional Dissertation, 2021, pp. 1-71.
(Continued)

*Primary Examiner* — Jonathan M Dunlap
(74) *Attorney, Agent, or Firm* — Bayramoglu Law Offices LLC

(57) ABSTRACT

A shear testing system and method of thermo-seepage-mechanical field and engineering disturbance coupling under deep and complex condition are provided. The shear testing system can be used in conjunction with an axial pressure application device to simplify the structure, save costs, and facilitate a triaxial confining pressure—temperature—axial pressure—torsional shear coupled test on a rock specimen. The shear testing system can achieve the following three purposes. First, the shear testing system can convert an axial pressure into a torsional shear force through a transmission mechanism of a power conversion assembly. Second, the shear testing system can apply an axial pressure
(Continued)

to the rock specimen fixed between two specimen fixing heads, through a pressure shaft of an axial pressure mechanism. Third, the shear testing system can apply a triaxial confining pressure and a temperature field to the rock specimen.

20 Claims, 13 Drawing Sheets

(51) Int. Cl.
*G01N 3/16* (2006.01)
*G01N 33/24* (2006.01)
(52) U.S. Cl.
CPC ............ *G01N 2203/0025* (2013.01); *G01N 2203/0026* (2013.01); *G01N 2203/0037* (2013.01); *G01N 2203/0067* (2013.01); *G01N 2203/0222* (2013.01); *G01N 2203/0256* (2013.01)
(58) Field of Classification Search
CPC ... G01N 2203/0026; G01N 2203/0037; G01N 2203/0067; G01N 2203/0222; G01N 2203/0256
See application file for complete search history.

(56) References Cited

U.S. PATENT DOCUMENTS

| | | | |
|---|---|---|---|
| 10,012,577 B2 * | 7/2018 | Zhou | G01N 33/24 |
| 10,684,203 B2 * | 6/2020 | Zhou | G01N 3/10 |
| 10,809,169 B2 * | 10/2020 | Ma | G01N 3/32 |
| 11,448,576 B2 * | 9/2022 | Li | E21B 44/04 |
| 2016/0108719 A1 | 4/2016 | Danisch | |
| 2018/0136099 A1 * | 5/2018 | Zhou | G01N 33/24 |
| 2019/0011344 A1 * | 1/2019 | Zhou | G01N 3/10 |
| 2020/0124510 A1 * | 4/2020 | Ma | G01N 3/32 |
| 2020/0386659 A1 * | 12/2020 | Li | E21B 49/02 |
| 2022/0119234 A1 | 4/2022 | Jiang | |

FOREIGN PATENT DOCUMENTS

| | | |
|---|---|---|
| CN | 206710226 U | 12/2017 |
| CN | 110044711 A | 7/2019 |
| CN | 114486522 A | 5/2022 |
| CN | 114791393 A | 7/2022 |
| CN | 115046848 A | 9/2022 |
| CN | 115420619 A | 12/2022 |
| CN | 116067803 A | 5/2023 |
| GB | 560469 A | 4/1944 |
| JP | 2006064404 A | 3/2006 |
| JP | 2007146783 A | 6/2007 |
| JP | 2008275404 A | 11/2008 |
| RU | 32601 U1 | 9/2003 |

OTHER PUBLICATIONS

Wei Demin, et al., Lead Rubber Bearing Model Considering Axial Effect, Journal of South China University of Technology (Natural Science Edition), 2008, pp. 1-5, vol. 36, No. 10.

X. Lu, et al., Shear modulus of porcine coronary artery: contributions of media and adventitia, Am J Physiol Heart Circ Physiol, 2003, pp. H1966-H1975, vol. 285.

* cited by examiner

SHEAR TESTING SYSTEM OF THERMO-SEEPAGE-MECHANICAL FIELD AND ENGINEERING DISTURBANCE COUPLING UNDER DEEP AND COMPLEX CONDITION

CROSS-REFERENCE TO THE RELATED APPLICATIONS

This application is based upon and claims priority to Chinese Patent Application No. 202311000134.9, filed on Aug. 10, 2023, the entire contents of which are incorporated herein by reference.

TECHNICAL FIELD

The present disclosure belongs to the technical field of rock testing, and in particular relates to a shear testing system and method of thermo-seepage-mechanical field and engineering disturbance coupling under deep and complex condition.

BACKGROUND

In the construction of underground rock engineering, the rock mass is typically subjected to a combined action of multiple complex stresses. For example, in addition to axial compression, the rock mass may be subjected to other effects such as shear stress, confining pressure, and seepage. Therefore, acquiring the shear strength parameters of rocks under axial compression is one of the measures to ensure the safety and reliability of rock engineering construction. At present, according to relevant testing specifications, the methods for testing rock shear strength parameters mainly include direct shear test, angle-varied plate shear test, and triaxial compression test, etc., each of which has its own advantages and disadvantages. The direct shear test requires a dedicated bidirectional loading testing machine and a determined shear load direction. A failure can only occur along the determined shear load direction, not necessarily along the direction resisting to the minimum shear stress. The angle-varied plate shear test is suitable for all material compression testing machines, but it faces the same problems as the direct shear test and needs to correct the friction coefficient of the angle-varied plate. The triaxial compression test requires a dedicated triaxial compression testing machine and involves a complex stress state of the rock and complex testing and analysis processes. These shear test methods can ultimately acquire the shear strength parameters for the failure of the rock, but due to the complex stress state inside the rock during testing, they cannot acquire the pure shear stress on the rock.

In fact, pure shear stress has important value in studying rock engineering failure. Laboratories engaged in engineering construction or scientific research typically have a material testing system (MTS) that can provide an axial pressure, such as a material compression testing machine. On this basis, Chinese patent application CN104297027A provides a rock specimen for pure shear testing and a pure shear testing method thereof in order to make all material compression testing machines available for pure shear testing. However, this method cannot acquire the pure shear angle.

In order to conduct pure shear testing of rocks, the existing torsional shear testing devices are specially designed and produced devices that can provide a torsional shear force. However, the various torsional shear testing devices for pure shear testing have at least one of the following drawbacks: (1) the torsional shear testing devices can only be used for pure shear testing, and the testing function is too single, (2) the rotation shaft for applying the torsional shear force during the torsional shear process is fixed, which causes a change in the force arm, making it unable to apply a linear torsional load, (3) the torsional shear testing devices require special design and production, resulting in significant costs and large footprints in the laboratory space, (4) the torsional shear testing devices cannot directly be used on existing testing machines, (5) the torsional shear testing devices need supporting peripheral facilities in case of complex coupling conditions, such as triaxial loading, seepage, and heating, (6) it is not easy for these torsional shear testing devices to test the torsional shear change by means of a strain method or acoustic emission, etc., (7) the torsional shear testing devices cannot ensure constant or controllable axial loads.

For example, Chinese patent application CN108152147A provides a torsional failure experimental device for a rock specimen, including a main frame. Upper and lower crossbeams of the main frame are respectively provided with a main hydraulic cylinder group and a double-rod hydraulic cylinder group for applying a pressure to the rock specimen. An end of a main piston rod of the main hydraulic cylinder group passing through the upper crossbeam is provided with a load transducer. A lower surface of the upper crossbeam is provided with an anti-rotation mechanism, which directly faces the main piston rod and restricts the rotation of the load transducer and the main piston rod. The anti-rotation mechanism is provided with an upper specimen pressure element with a groove matched to the rock specimen. One end of an auxiliary piston rod of the double-rod hydraulic cylinder group passes through the lower crossbeam and is provided with a lower specimen pressure element. The lower specimen pressure element is provided with a groove that is matched to the groove of the upper specimen pressure element to clamp the rock specimen. The other end of the auxiliary piston rod passes through an auxiliary cylinder body and is provided with a bearing. One side of the lower crossbeam is provided with a power output mechanism for applying a torque to the rock specimen. The power output mechanism is connected to a connecting shaft through a transmission mechanism. The connecting shaft is provided with a torque transducer. The other end of the torque transducer is fixedly connected to the end of the auxiliary piston rod with the bearing. The torque transducer, the load transducer, the main hydraulic cylinder group, the double-rod hydraulic cylinder group, and the power output mechanism are all connected to a control module.

In the torsional failure experimental device for a rock specimen, the main hydraulic cylinder group and the double-rod hydraulic cylinder group are configured to apply an axial pressure to the rock specimen. The power output mechanism is connected to the connecting shaft through the transmission mechanism and is configured to apply a torque to the rock specimen. In this way, the torsional failure experimental device can be used to study the deformation and failure of a rock that is subjected to an axial pressure and a torsional shear force simultaneously. However, undoubtedly the torsional failure experimental device has high complexity and large size. In addition, the torsional failure experimental device cannot convert an axial pressure into a torsional shear force, so it cannot be used in conjunction with an axial pressure application device. For this reason, the torsional failure experimental device requires separate design and production of the main hydraulic cylinder group and the double-rod hydraulic cylinder group for providing the axial pressure and requires separate design and production of the power output mechanism for providing the torsional shear force. This undoubtedly increases device costs and occupies extra laboratory space. Furthermore, the torsional failure experimental device lacks a mechanism for applying a triaxial confining pressure, a temperature field, and a seepage field. Therefore, it is not easy for the torsional failure experimental device to conduct a triaxial confining pressure—axial pressure—torsional shear coupled test, a triaxial confining pressure—temperature—axial pressure—torsional shear coupled test, a triaxial confining pressure—axial pressure—seepage—torsional shear coupled test, or a triaxial confining pressure—temperature—axial pressure—seepage—torsional shear coupled test on the rock specimen.

SUMMARY

The present disclosure provides a shear testing system of thermo-seepage-mechanical field and engineering disturbance coupling under deep and complex condition. The shear testing system can be used in conjunction with an axial pressure application device to simplify the structure, save costs, and facilitate a triaxial confining pressure—temperature—axial pressure—torsional shear coupled test on a rock specimen.

The present disclosure solves the technical problems with the following technical solutions. A shear testing system of thermo-seepage-mechanical field and engineering disturbance coupling under deep and complex condition includes a device body and a specimen fixing mechanism, where the device body is provided therein with a working chamber;
the specimen fixing mechanism includes two specimen fixing heads that are arranged opposite in the working chamber; and corresponding positions of the two specimen fixing heads are respectively provided with specimen fixing parts;
the shear testing system further includes a triaxial cell;
the device body is provided with a first mounting position and a second mounting position that are respectively corresponding to the two specimen fixing heads; the first mounting position and/or the second mounting position of the device body are provided with a power conversion assembly; and the power conversion assembly includes a torque output component, a power input component, a transmission mechanism, and an axial pressure mechanism;
the torque output component is rotatably provided on the device body, fixedly connected to the corresponding specimen fixing head, and able to drive the specimen fixing head to rotate relative to the other specimen fixing head;
the power input component is linearly movable;
the transmission mechanism is in transmission connection with the torque output component and the power input component, and is able to convert a linear motion of the power input component into a rotational motion of the torque output component;
the axial pressure mechanism includes a pressure shaft slidably provided inside the power input component; an inner end of the pressure shaft sequentially passes through an inner end of the power input component, the torque output component, and the upper specimen fixing head connected to the torque output component, and extends to the specimen fixing part of the upper specimen fixing head; and an outer end of the pressure shaft is provided with a sliding groove;
the axial pressure mechanism further includes a piston that is slidably provided in the sliding groove of the pressure shaft and forms a pressure chamber with the sliding groove; the pressure chamber is filled with a pressure medium; and the pressure medium is configured to generate a pressure to make an outer end surface of the piston flush with an outer end surface of the power input component; and
an inner chamber of the triaxial cell forms a triaxial pressure chamber; the triaxial cell is provided with a pressure rod through-hole for a pressure rod to penetrate into the triaxial pressure chamber; the device body is located in the triaxial pressure chamber; and there is at least one power input component corresponding to the pressure rod through-hole.

Further, the device body includes a device base, support rods provided on the device base, and a device cover provided on top ends of the support rods; and the working chamber is a space between the device base and the device cover.

Further, the support rods are telescopic support rods with an adjustable length; and there are at least three support rods distributed in a ring array.

Further, the axial pressure mechanism further includes a pressure medium inlet tube and a pressure medium outlet tube that are communicated with the pressure chamber, as well as a clamp projection provided in the sliding groove of the pressure shaft for limiting the piston.

Further, the shear testing system includes a pressure shaft pressurization module and a confining pressure field module;

the pressure shaft pressurization module includes a pressure medium outlet connected to the pressure medium inlet tube and a pressure medium inlet connected to the pressure medium outlet tube; and
the confining pressure field module includes a confining pressure medium outlet communicated with a pressurization port of the triaxial cell and a confining pressure medium inlet communicated with a pressure relief port of the triaxial cell.

Further, the two specimen fixing heads include an upper specimen fixing head and a lower specimen fixing head that are arranged above and below;

the first mounting position of the device body is corresponding to the upper specimen fixing head, and only the first mounting position is provided with the power conversion assembly;
the lower specimen fixing head is fixedly connected to the device base;
the torque output component is annular in shape;
the power input component is coaxial with the torque output component; and
the transmission mechanism includes a gear ring located on a top surface of the torque output component and surrounding the power input component, gear racks located on the power input component and distributed along a centerline of a motion trajectory of the power input component, and shaft gears rotatably provided on the device body and engaged with the gear ring and the gear racks, respectively.

Further, an upper seepage channel is provided in the upper specimen fixing head and/or the pressure shaft; and the upper seepage channel includes a first upper seepage fluid access opening located at a lower end of the pressure shaft and a second upper seepage fluid access opening located on a side wall of the pressure shaft or a side wall of the upper specimen fixing head; and the lower specimen fixing head is provided therein with a lower seepage channel; and the lower seepage channel includes a first lower seepage fluid access opening located at the specimen fixing part of the lower specimen fixing head and a second lower seepage fluid access opening located on a side wall of the lower specimen fixing head.

Further, the power input component is provided with a power input terminal at an outer side of the device body; and a surface of the power input terminal forms the outer end surface of the power input component; and the power input component is provided with a reset plate; the reset plate is located at an upper side of the device cover; and a reset spring is provided between the reset plate and the device cover.

Further, the power input component is rectangular in shape, with the gear racks on all four sides; and there are four shaft gears respectively engaged with the gear racks on the four sides of the power input component.

Further, a bottom plate of the triaxial cell forms a test bed; and the device body is fixed to the test bed.

The present disclosure further provides a shear testing method of thermo-seepage-mechanical field and engineering disturbance coupling under deep and complex condition, for rock testing by a shear testing system, where the shear testing system is the above-mentioned shear testing system of thermo-seepage-mechanical field and engineering disturbance coupling under deep and complex condition, and the shear testing method includes the following steps:

step 1: preparing a rock specimen; wrapping the rock specimen with a sealing film that includes two ends sealed by sealing rings, respectively; and fixing the rock specimen between the upper specimen fixing head and the lower specimen fixing head of the shear testing system;

step 2: mounting the shear testing system with the fixed rock specimen on an axial pressure application device; communicating the pressure chamber with the pressure shaft pressurization module in a cyclic manner, communicating the triaxial pressure chamber with the confining pressure field module in a cyclic manner, and electrically connecting the heating element to the temperature field module; making the pressure rod of the axial pressure application device just in contact with the outer end surface of the piston; and controlling an amount of the pressure medium injected into the pressure chamber to apply a constant axial pressure to the rock specimen;

step 3: driving, by the axial pressure application device, the power input component and the piston to move linearly; converting, by the transmission mechanism, the linear motion of the power input component into a rotational motion of the torque output component; driving, by the torque output component, the upper specimen fixing head fixedly connected to the torque output component to rotate relative to the lower specimen fixing head, thereby applying a torque to the rock specimen; causing the piston and the power input component to move axially synchronously; and controlling, by the pressure shaft pressurization module, the amount of the pressure medium injected into the pressure chamber, so as to maintain a constant axial pressure applied to the rock specimen or to ensure that the axial pressure applied to the rock specimen changes as expected for testing; and injecting, by the confining pressure field module, test oil into the triaxial pressure chamber to apply a triaxial confining pressure to the rock specimen; and controlling, by the temperature field module, the heating element to heat the test oil and the rock specimen; and step 4: subjecting the rock specimen to a triaxial confining pressure—temperature—axial pressure—torsional shear coupled test; measuring a deformation and failure of the rock specimen during the test; and acquiring data for analysis.

The present disclosure has following beneficial effects:

1) In the shear testing system, the power conversion assembly is mounted at the first mounting position and/or the second mounting position of the device body. The power input component of the power conversion assembly is linearly movable, so it can coordinate axially with the pressure rod of the axial pressure application device to take the axial pressure provided by the axial pressure application device as power. The linear motion of the power input component is converted into the rotational motion of the torque output component through the transmission mechanism of the power conversion assembly, and the torque output component drives the specimen fixing head fixedly connected to it to rotate relative to the other specimen fixing head. In this way, the torque is applied to the rock specimen fixed between the two specimen fixing heads for testing.

The pressure shaft of the axial pressure mechanism is slidably provided in the power input component. The pressure shaft includes an inner end extending to the specimen fixing part and an outer end provided with a sliding groove for sliding of the piston. The pressure chamber formed by the piston and the sliding groove is filled with a pressure medium that can make an outer end surface of the piston flush with an outer end surface of the power input component. The pressure rod of the axial pressure application device can act simultaneously on the outer end surface of the piston and the outer end surface of the power input component, that is, the pressure rod can drive both the power input component and the piston of the axial pressure mechanism. The motion of the piston inevitably drives the pressure medium to push the pressure shaft, such that the axial pressure is applied to the rock specimen fixed between the two specimen fixing heads through the pressure shaft of the axial pressure mechanism for testing.

The device body is located in the triaxial pressure chamber of the triaxial cell, and the test oil is injected into the triaxial pressure chamber to apply a triaxial confining pressure to the rock specimen fixed between the two specimen fixing heads for testing. There is a heating element in the triaxial pressure chamber, which can heat the test oil and the rock specimen to apply a temperature field for testing.

The shear testing system can convert the axial pressure into a torsional shear force, apply the axial pressure to the rock specimen through the pressure shaft, and apply the triaxial confining pressure and the temperature field to the rock specimen. Therefore, it can test a rock specimen subjected to both an axial pressure and a torsional shear force with the help of only the axial pressure application device, without the need for a dedicated dynamic mechanism to provide the torsional shear force. Compared with existing rock testing devices with the same function, the shear testing system features a simple structure, low production cost, and less laboratory space occupation, and is convenient for conducting a triaxial confining pressure—temperature—axial pressure—torsional shear coupled test on the rock specimen.

2) The shear testing system can be used in conjunction with the axial pressure application device. Therefore, the whole shear testing system as a whole can serve as a test object and can be tested by an existing testing machine, expanding the testing functions of existing testing machines.

3) The shear testing system can convert the linear motion of the power input component into the rotational motion of the torque output component through the transmission mechanism with the shaft gears simultaneously engaged with the gear ring and the gear racks. The power can be input and output at the two ends within a shorter transmission distance. The shear testing system has a simple and compact overall structure and small volume, and eliminates the need for a new testing machine, saving a lot of costs and space.

4) The shear testing system can maintain a constant force arm during the torsional shear process through the transmission mechanism with the shaft gears simultaneously engaged with the gear ring and the gear racks, ensuring that the torsional load is linearly applied.

5) The shear testing system is communicated with the seepage fluid access opening of the seepage field module through the upper seepage channel and the lower seepage channel to form a seepage circuit, which facilitates the test of the rock specimen under a seepage condition, such as a triaxial confining pressure—seepage—torsional shear coupled test or a triaxial confining pressure—axial pressure—seepage—torsional shear coupled test.

6) The shear testing system is easy to test the rock specimen using both a strain method and an acoustic emission method.

7) The shear testing system can directly utilize the peripheral facilities such as temperature field module, confining pressure field module, seepage field module of existing testing machines for coupled tests, without the need for redesign and production, further reducing costs.

8) The amount of the pressure medium in the pressure chamber is controlled to achieve a constant or regular change in the pressure, such that the axial pressure applied to the rock specimen remains constant or controllable for a torsional shear test under a constant pressure or a variable pressure.

Figure 1:
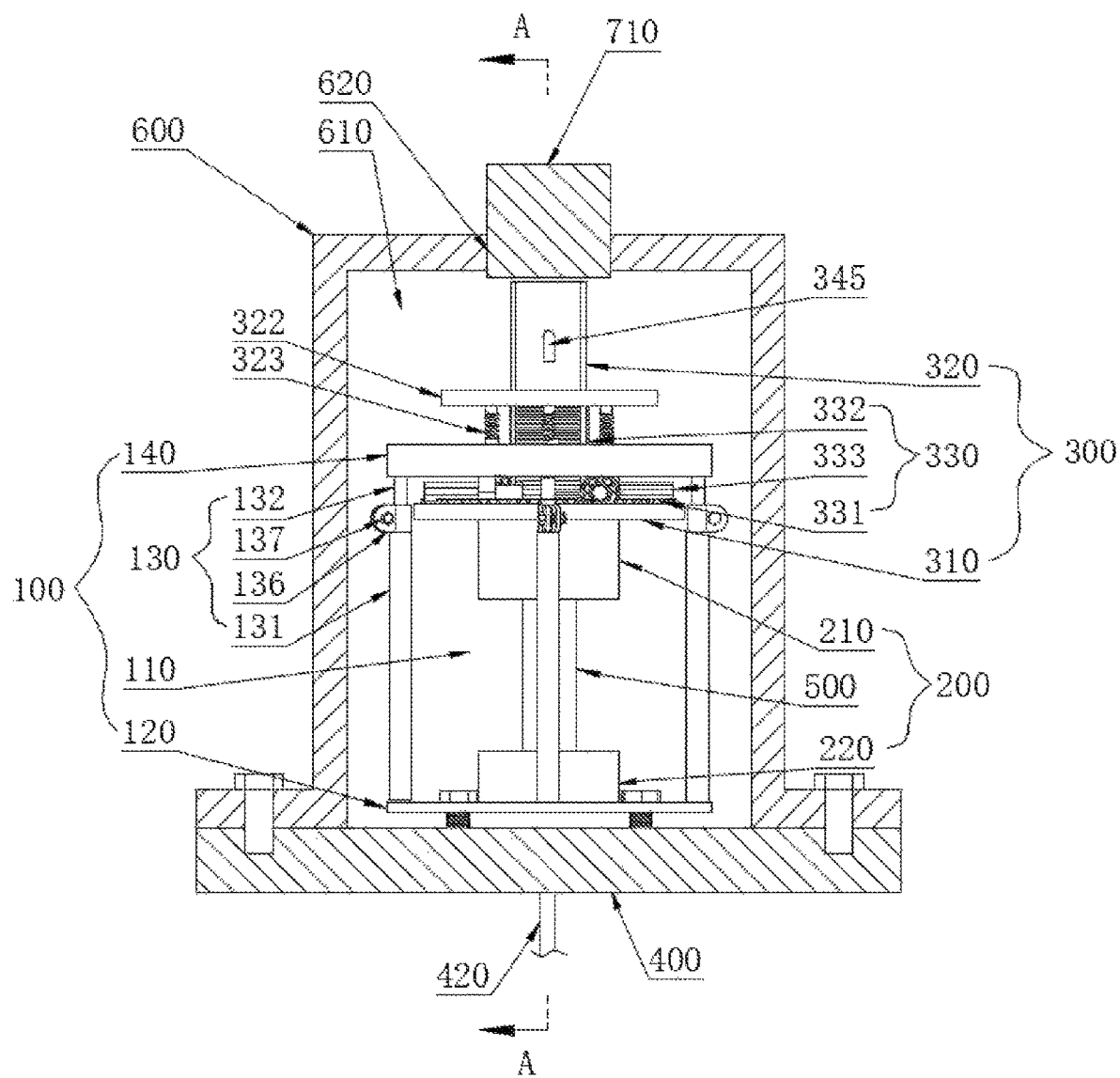
FIG. 1 is an implementation diagram of a shear testing system of thermo-seepage-mechanical field and engineering disturbance coupling under deep and complex condition according to the present disclosure.

Reference Numerals: 100. device body; 110. working chamber; 120. device base; 130. support rod; 131. telescopic rod sleeve; 132. telescopic rod body; 136. ring clamp; 137. second locking element; 138. elastic inner ring; 140. device cover; 200. specimen fixing mechanism; 210. upper specimen fixing head; 220. lower specimen fixing head; 230. sealing joint; 231. sealing joint body; 232. sealing connection end; 233. end sealing ring; 240. water injection joint; 241. water injection joint body; 242. conical end 243. joint shoulder; 244. joint connecting sleeve; 300. power conversion assembly; 310. torque output component; 320. power input component; 321. power input terminal; 322. reset plate; 323. reset spring; 330. transmission mechanism; 331. gear ring; 332. gear rack; 333. shaft gear; 340. axial pressure mechanism; 341. pressure shaft; 342. piston; 343. pressure chamber; 344. pressure medium inlet tube; 345. pressure medium outlet tube; 346. clamp projection; 400. test bed; 410. oil filling tube; 420. oil return tube 500. rock specimen; 510. sealing film; 520. sealing ring; 600. triaxial cell; 610. triaxial pressure chamber; 620. pressure rod through-hole; 710. pressure rod; 810. torque transducer mounting seat; 820. torque transducer; 830. angle transducer mounting seat; 840. angle transducer; 841. angle transducer body; 842. angle transducer upper-end pointer; and 843. angle transducer lower-end pointer.

DETAILED DESCRIPTION OF THE EMBODIMENTS

The present disclosure will be further described below with reference to the drawings.

It should be explained that in the description of the present disclosure, terms such as "upper", "lower", "top", "bottom", "inside", and "outside" indicate the orientation or positional relationships based on the drawings. They are merely intended to facilitate the description of the present disclosure, rather than to indicate or imply that the mentioned device or component must have a specific orientation or must be constructed and operated in a specific orientation. Therefore, these terms should not be construed as a limitation to the present disclosure. The expression "mainly include" can be interpreted as including a structural component not mentioned in herein. The term "and/or" herein merely describes three types of associations between associated objects. For example, "A and/or B" means "A alone", "A and B", or "B alone". Moreover, terms such as "first" and "second" are merely intended for the purpose of description, and should not be construed as indicating or implying relative importance.

Figure 2:
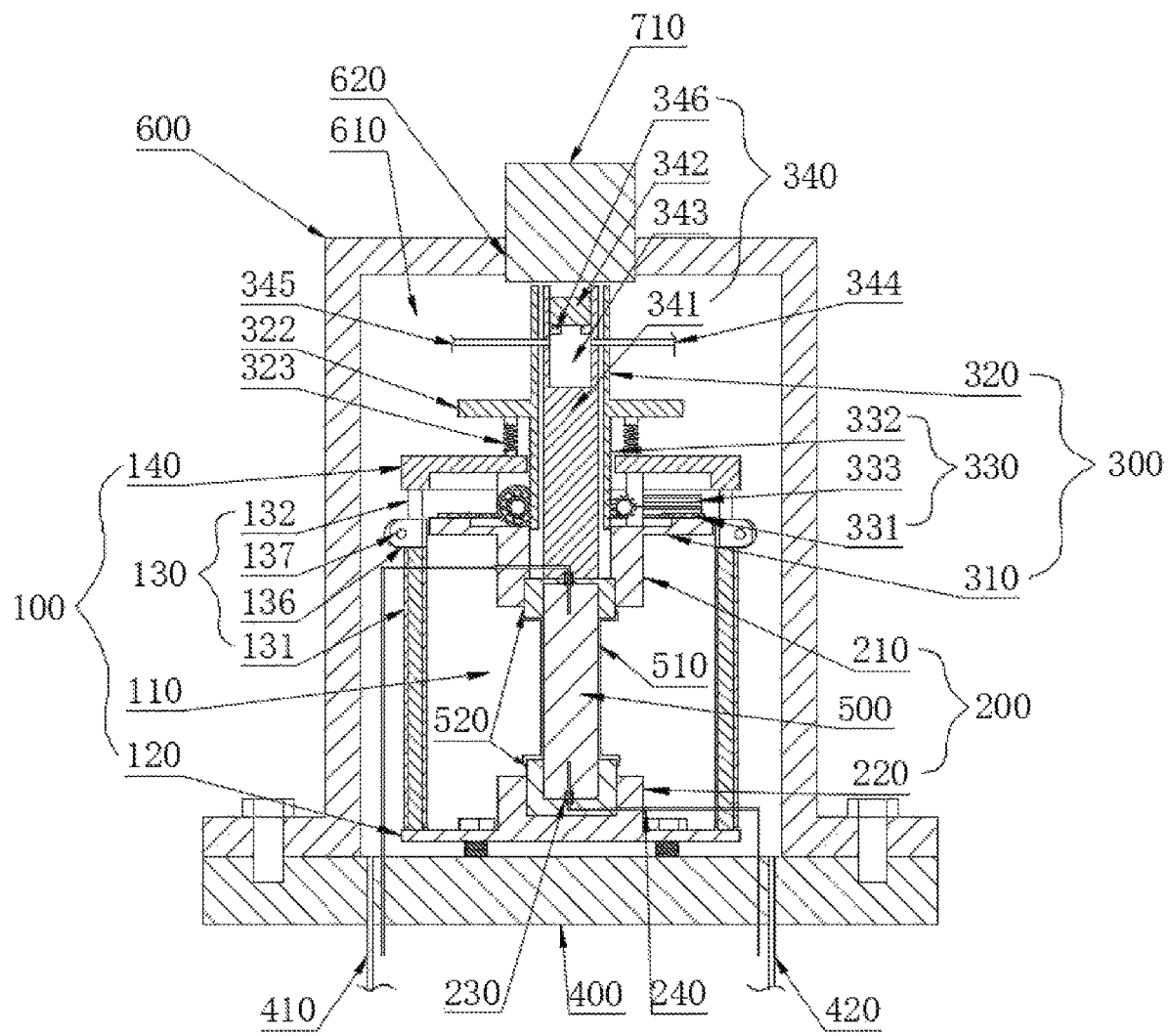
FIG. 2 is a sectional view taken along A-A shown in FIG. 1.
Figure 3:
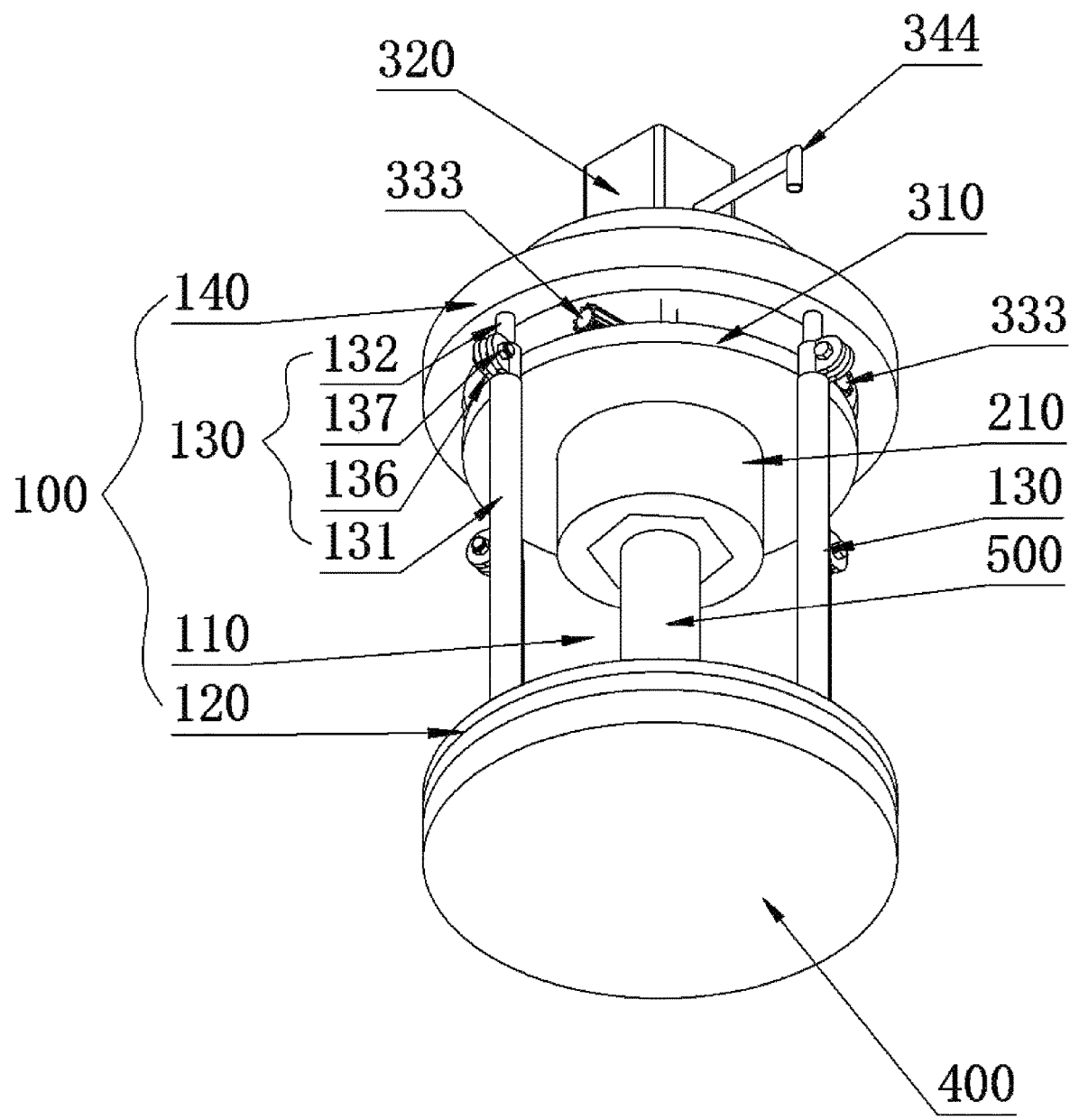
FIG. 3 is a three-dimensional structural diagram of a device body.

As shown in FIGS. 1, 2, and 3, a shear testing system of thermo-seepage-mechanical field and engineering disturbance coupling under deep and complex condition includes device body 100, specimen fixing mechanism 200, and triaxial cell 600.

The device body 100 is a main component of the shear testing system, and is provided therein with working chamber 110. The working chamber 110 is a space for storing rock specimen 500 and conducting a test.

Figure 10:
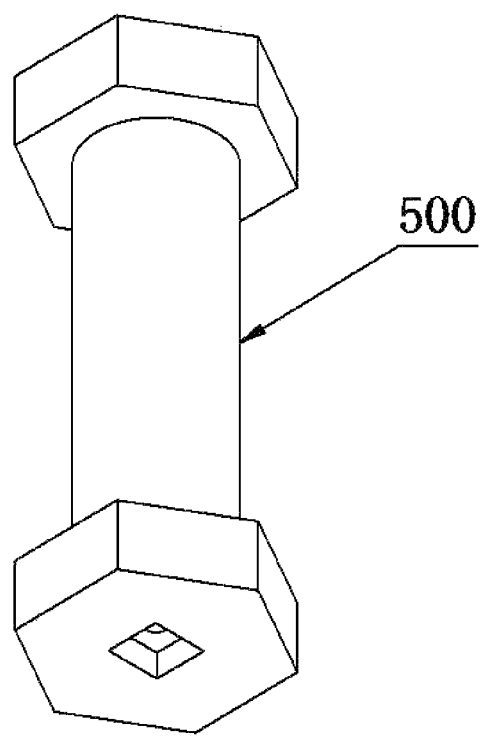
FIG. 10 is a structural diagram of a solid cylindrical rock specimen.

The specimen fixing mechanism 200 is mainly configured to mount and fix the rock specimen 500 for a test. The rock specimen 500 can have various structural forms, and can be, for example, solid cylindrical rock specimen 500 shown in FIG. 10, hollow cylindrical rock specimen 500 shown in FIG. 11, solid square-columnar rock specimen 500 shown in FIG. 12, and hollow square-columnar rock specimen 500 shown in FIG. 13. The specimen fixing mechanism 200 includes two specimen fixing heads arranged opposite in the working chamber 110. Corresponding parts of the two specimen fixing heads are respectively provided with specimen fixing parts. The specimen fixing parts can have multiple structures to fix ends of the rock specimen 500. Preferably, the specimen fixing parts are specimen fixing grooves, each with a regular polygonal cross-section. In this case, typically, fixing joints matched to specimen fixing grooves are adhered to the ends of the rock specimen 500. Alternatively, the ends of the rock specimen 500 are processed into structures matched and fixed to the specimen fixing grooves. For example, in an implementation shown in FIG. 3, the specimen fixing parts are regular hexagonal specimen fixing grooves, and hexagonal joints matched and fixed to the regular hexagonal specimen fixing grooves are typically adhered to the ends of the rock specimen 500. In an implementation shown in FIG. 12, the specimen fixing parts are regular quadrilateral specimen fixing grooves, which can directly be matched and fixed to the ends of the solid square-columnar rock specimen 500. For hollow rock specimen 500, protrusions can typically be provided in the specimen fixing grooves or connecting grooves of the fixing joints to match ends of an inner cavity of the rock specimen 500, so as to increase an adhesive area. For example, in an implementation shown in FIG. 11, protrusions are provided in the connecting grooves of the fixing joints. In an implementation shown in FIG. 13, the specimen fixing parts are regular quadrilateral specimen fixing grooves with protrusions in a center.

The device body 100 is provided with a first mounting position and a second mounting position that are respectively corresponding to the two specimen fixing heads. The first mounting position and/or the second mounting position of the device body 100 are provided with power conversion assembly 300. The power conversion assembly 300 includes torque output component 310, power input component 320, transmission mechanism 330, and axial pressure mechanism 340.

The torque output component 310 is rotatably provided on the device body 100, fixedly connected to the corresponding specimen fixing head, and able to drive the specimen fixing head to rotate relative to the other specimen fixing head. The torque output component 310 is mainly configured to apply a torque to the rock specimen 500. The torque output component 310 is rotatably provided on the device body 100 in various ways. For example, the torque output component may be rotatably matched to the device body 100 through a rotation shaft, the torque output component 310 may be rotatably supported on the device body 100 through a thrust ball bearing, and the torque output component 310 with an annular circumference may be rotatably provided in an annular groove of the device body 100.

When only one specimen fixing head is connected to the torque output component 310, the other specimen fixing head is typically fixedly connected to a stationary component relative to the torque output component 310, and is preferably fixedly connected to the device body 100. When the two specimen fixing heads are respectively connected to two torque output components 310, only a rotational difference is needed between the two torque output components 310 to make the two specimen fixing heads rotatable relative to each other. For example, two power conversion assemblies 300 are respectively arranged in the first mounting position and the second mounting position of the device body 100. When centerlines of motion trajectories of the power input components 320 of two power conversion assemblies 300 are parallel to each other, transmission ratios of transmission mechanisms 330 of the two power conversion assemblies 300 are different, thereby resulting in the rotational difference between the two torque output components 310.

The power input component 320 is movably provided and is linearly movable. The power input component 320 is mainly configured to be axially matched to a pressure rod of an axial pressure application device, so as to use the axial pressure provided by the device as power. The power input component 320 is movably provided on a mounting bracket thereof or on the device body 100. The mounting bracket or the device body 100 is typically provided a structure for limiting the power input component 320 to ensure that the power input component is linearly movable. Typically, the power input component 320 is vertically centered. A circumferential contour size of the power input component 320 is smaller than a size of a center opening of a device cover or base of the device body 100 or the torque output component 310, so as to ensure that the power input component 320 is freely and stably movable up and down in the event of engagement through the transmission mechanism 330 or transmission through a thread.

The transmission mechanism 330 is in transmission connection with the torque output component 310 and the power input component 320, and converts a linear motion of the power input component 320 into a rotational motion of the torque output component 310. The transmission mechanism 330 can take various forms, such as pinion and rack mechanism, ball screw mechanism, cam mechanism, crank connecting rod mechanism, and lever mechanism.

The axial pressure mechanism 340 is mainly configured to apply an axial pressure to the rock specimen 500 fixed between the two specimen fixing heads. The axial pressure mechanism 340 includes pressure shaft 341 slidably provided inside the power input component 320. An inner end of the pressure shaft 341 sequentially passes through an inner end of the power input component 320, the torque output component 310, and the specimen fixing head connected to the torque output component 310, and extends to the specimen fixing part. An outer end of the pressure shaft 341 is provided with a sliding groove. Typically, the power input component 320 is provided therein with a guide groove that is formed along a motion trajectory of the power input component for sliding of the pressure shaft 341. The pressure shaft 341 is slidably provided inside the guide groove. The inner end of the pressure shaft 341 is mainly in contact with the end of the rock specimen 500, and the outer end of the pressure shaft 341 is provided with the sliding groove to reserve space for adjusting a stroke of the pressure shaft 341. In this way, when there is a stroke difference between the pressure shaft 341 and the power input component 320, the axial pressure mechanism 340 and the power input component 320 can use the same axial pressure as power.

The axial pressure mechanism 340 further includes piston 342 that is slidably provided in the sliding groove of the pressure shaft 341 and forms pressure chamber 343 with the sliding groove. The pressure chamber 343 is filled with a pressure medium. A pressure generated by the pressure medium can make the outer end surface of the piston 342 flush with the outer end surface of the power input component 320. When the shear testing system simultaneously applies an axial pressure and a torsional shear force to the rock specimen 500, the stroke of the pressure shaft 341 is often smaller than a stroke of the dynamic input component 320. The pressure medium is provided in the pressure chamber 343 to achieve the following purposes. Firstly, the axial pressure received by the piston 342 is transmitted to the pressure shaft 341 through the pressure of the pressure medium, so as to apply the axial pressure to the rock specimen 500 fixed between the two specimen fixing heads through the pressure shaft 341. Secondly, the stroke difference between the pressure shaft 341 and the power input component 320 is eliminated by discharging or compressing the pressure medium. Specifically, the stroke of the piston 342 is the same as the stroke of the power input component 320. When the stroke of the pressure shaft 341 is smaller, the pressure medium is squeezed by the pressure shaft 341 and the piston 342, causing the pressure medium to be partially discharged or compressed into a smaller volume to achieve stroke elimination. Thirdly, an operator can control the magnitude of the axial pressure applied by the pressure shaft 341 to the rock specimen 500 by controlling the amount of the pressure medium in the pressure chamber 343.

An inner chamber of the triaxial cell 600 forms triaxial pressure chamber 610. The triaxial cell 600 is provided with pressure rod through-hole 620 for pressure rod 710 to penetrate into the triaxial pressure chamber 610. The triaxial pressure chamber 610 is provided therein with a heating element. The device body 100 is located in the triaxial pressure chamber 610, and at least one power input component 320 is corresponding to the pressure rod through-hole 620. The triaxial cell 600 is mainly configured to inject test oil into the triaxial pressure chamber 610 so as to apply a triaxial confining pressure on the rock specimen 500 fixed between the two specimen fixing heads. The triaxial cell 600 is typically provided with a pressurization port and a pressure relief port communicated with the triaxial pressure chamber 610. The pressurization port is typically connected to oil filling tube 410, and the pressure relief port is typically connected to oil return tube 420, so as to inject and discharge the test oil. The heating element is mainly configured to heat the test oil and the rock specimens 500 so as to apply a temperature field. The heating element can take various forms, such as electric heating wire, heating rod, and heating tube.

The shear testing system can simulate complex deep underground conditions and perform at least a pure torsional shear test, a torsional shear test under a constant pressure, a torsional shear test under a variable pressure, a triaxial confining pressure—axial pressure—torsional shear coupled test, and a triaxial confining pressure—temperature—axial pressure—torsional shear coupled test.

Specifically, in the implementations shown in FIGS. 1, 2, and 3, the device body 100 includes device base 120, support rods 130 provided on the device base 120, and device cover 140 provided on top ends of the support rods 130. The working chamber 110 is a space between the device base 120 and the device cover 140. The device body 100 features a simple structure and convenient production. The support rods 130 support the device cover 140, and multiple openings are formed at a side of the working chamber 110 to facilitate the disassembly and assembly of the rock specimen 500 by the operator. Typically, only one operator is needed to carry out the test.

In order to improve the overall structural strength of the device body 100 and the stability of the support rods 130 supporting the device cover 140, as shown in FIG. 3, in another implementation of the device body 100, there are at least three support rods 130 distributed in a ring array based on the above implementation.

The two specimen fixing heads can be arranged in various directions within a spatial range in the working chamber 110. In order to facilitate the fixation of the rock specimen 500 and improve the testing accuracy, preferably, the two specimen fixing heads are arranged vertically or horizontally, that is, the two specimen fixing heads are coaxial and axial vertically or horizontally. For example, in the implementations shown in FIGS. 1 to 3, the two specimen fixing heads are arranged vertically.

For the convenience of testing different rock specimens 500 with varying lengths, as shown in FIGS. 1, 2, and 3, preferably, the support rod 130 is a telescopic support rod with an adjustable length, and the two specimen fixing heads include upper specimen fixing head 210 and lower specimen fixing head 220 that are arranged above and below. A relative distance between the first mounting position and the second mounting position of the device body 100 is adjustable by adjusting the length of the support rod 130. The first mounting position and/or the second mounting position are provided with the power conversion assembly 300, and the torque output component 310 of the power conversion assembly 300 is fixedly connected to the corresponding upper specimen fixing head 210 or lower specimen fixing head 220. Therefore, the relative distance between the upper specimen fixing head 210 and the lower specimen fixing head 220 is adjustable, such that different rock specimens 500 with varying lengths can be mounted between the upper specimen fixing head 210 and the lower specimen fixing head 220, which is very convenient for testing.

The support rod 130 in the telescopic form typically includes telescopic rod sleeve 131 and telescopic rod body 132 nested inside the telescopic rod sleeve, and can have multiple telescopic modes. For example, the support rod 130 may be telescopic through a spiral method, but in this case at least one end of the support rod 130 needs to be rotatably connected. Besides, a pneumatic or hydraulic system may be provided to make the support rod 130 telescopic, a linear motor may be provided to make the support rod 130 telescopic, and the support rod 130 may be telescopic by manual operation.

In order to facilitate the adjustment of the length of the support rod 130 and lock it in place, in the implementations shown in FIGS. 1, 2, and 3, the support rod 130 includes the telescopic rod sleeve 131 provided on the device base 120 and the telescopic rod body 132 nested inside the telescopic rod sleeve and movable along an axial direction of the telescopic rod sleeve 131. The telescopic rod sleeve 131 and/or the telescopic rod body 132 are provided with a locking structure that restricts the movement of the telescopic rod body 132. A top of the telescopic rod body 132 is the top of the support rod 130.

The locking structure is configured to lock and fix the support rod 130 after adjusting its length to maintain the support rod at that length, facilitating testing of the rock specimen 500 with the corresponding length. The locking structure can have multiple locking methods, such as threaded spiral locking, snap ring axial locking, and pin or screw locking.

As shown in FIGS. 1, 2, 3, and 5, in a preferred implementation, the locking structure includes a notch provided at an upper end of the telescopic rod sleeve 131, ring clamp 136 provided at the upper end of the telescopic rod sleeve 131, and second locking element 137 connected to two ends of the ring clamp 136. The locking structure has the following advantages. (1) Strong stability. When locking, the second locking element 137 can be twisted to firmly clamp the upper end of the telescopic rod sleeve 131 and the telescopic rod body 132 with the ring clamp 136, so as to prevent it from loosening and falling off (2) High convenience. The locking structure is convenient for mounting and disassembly, adjustable within a continuous length range, and flexible and easy to use, and can accommodate different rock specimens 500 with varying sizes. (3) High reliability. The locking structure can basically protect the support rod 130 from safety issues such as breakage or deformation during use.

As shown in FIG. 2, in a preferred solution of the present disclosure, the axial pressure mechanism 340 further includes pressure medium inlet tube 344 and pressure medium outlet tube 345 that are communicated with the pressure chamber 343, as well as clamp projection 346 provided in the sliding groove of the pressure shaft 341 for limiting the piston 342. The pressure medium inlet tube 344 and the pressure medium outlet tube 345 are respectively configured to carry out injection and discharge of the pressure medium in the pressure chamber 343 to control a pressure inside the pressure chamber 343, making it convenient for the operator to control the magnitude of the axial pressure applied by the pressure shaft 341 to the rock specimen 500. The clamp projection 346 is mainly configured to limit and support the piston 342, so as to prevent the piston 342 from entering the sliding groove too deeply when not in operation.

In another preferred solution of the present disclosure, the shear testing system further includes a pressure shaft pressurization module, a confining pressure field module, and a temperature field module. The pressure shaft pressurization module includes a pressure medium outlet connected to the pressure medium inlet tube 344 and a pressure medium inlet connected to the pressure medium outlet tube 345. The confining pressure field module includes a confining pressure medium outlet communicated with the pressurization port of the triaxial cell 600 and a confining pressure medium inlet communicated with the pressure relief port of the triaxial cell 600. The temperature field module includes a temperature field controller, a temperature field transducer, and a power supply. The temperature field transducer is provided in the triaxial pressure chamber, and the heating element, the temperature field transducer, and the power supply are all electrically connected to the temperature field controller.

The pressure shaft pressurization module mainly includes a container for holding the pressure medium, a pressurization pump, a flow meter, and a control valve. The pressure medium is injected into the pressure chamber 343 or discharged from the pressure chamber to control the magnitude of the axial pressure applied by the pressure shaft 341 to the rock specimen 500. The design facilitates the study of the mechanical behavior of the rock specimen 500 subjected to the axial pressure—torsional shear coupled action and acquisition of the mechanical parameters of the rock specimen, providing experimental basis and data support for rock engineering exploration and design. The pressure medium varies in different types, such as gas, water, and hydraulic oil.

Based on the pressure shaft pressurization module, a torsional shear test is conducted by the shear testing system under a constant axial pressure according to the following process and principle. After the rock specimen is prepared and mounted, first, test bed 400 is adjusted such that the pressure rod 710 of pressure testing machine just contacts the outer end surface of the piston 342 and an axial pressure transducer of the pressure testing machine shows data greater than zero. Then, hydraulic oil is injected into the pressure chamber 343 through the pressure medium inlet tube 344 to reach an expected axial pressure for the rock specimen 500. The hydraulic oil transmits a pressure to all sides. The piston 342 tends to slide outward and transfers the pressure to the pressure rod 710. The pressure shaft 341 tends to move inward and directly transmits an axial pressure to the end of the rock specimen 500. At this point, the operation of pre-applying a constant axial pressure to the rock specimen 500 is completed. During a subsequent torsional shear operation, the oil discharge state of the pressure medium outlet tube 345 is controlled through an overflow valve. When the pressure rod 710 of the pressure testing machine moves axially to apply the pressure, the piston 342 and the power input component 320 move synchronously axially. When the pressure generated by the hydraulic oil exceeds a set axial pressure, an oil discharge threshold of the pressure medium outlet tube 345 appears. The hydraulic oil is discharged into an oil tank through the pressure medium outlet tube 345, keeping the pressure transmitted by the hydraulic oil to all sides constant, so as to maintain a constant axial pressure applied by the pressure shaft 341 to the rock specimen 500.

The confining pressure field module mainly includes a high-pressure vessel, a pressure control system, and a pressure transducer. It can generate different confining pressures on the rock specimen 500 so as to study the mechanical behavior of the rock specimen and acquire its mechanical parameters. The confining pressure can be coupled with a torsional shear or coupled with an axial pressure and a torsional shear to further study the performance of the rock specimen in a complex environment and acquire corresponding parameters of the rock specimen, providing experimental basis and data support for rock engineering exploration and design.

The temperature field module carries out temperature control through a temperature field controller to generate different temperature fields on the rock specimen 500, thereby studying the mechanical behavior of the rock specimen and acquiring its mechanical parameters. The temperature field can be coupled with a confining pressure, an axial pressure, a seepage field, and a torsional shear to study the performance of the rock specimen in a complex environment and acquire corresponding parameters of the rock specimen, providing experimental basis and data support for rock engineering exploration and design.

Figure 8:
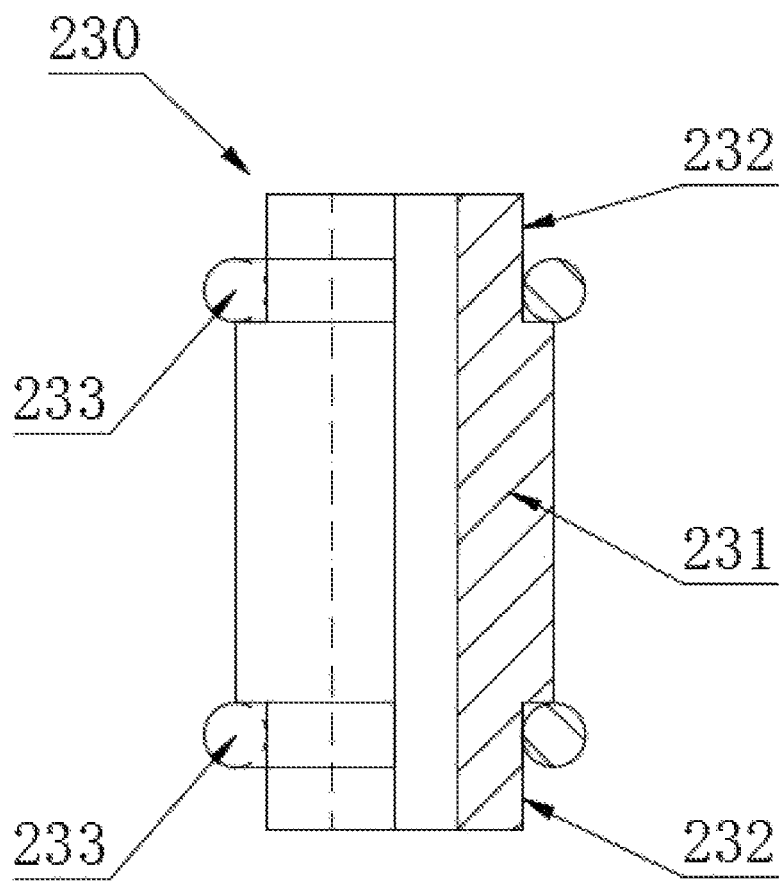
FIG. 8 is a semi-sectional view of a sealing joint.
Figure 9:
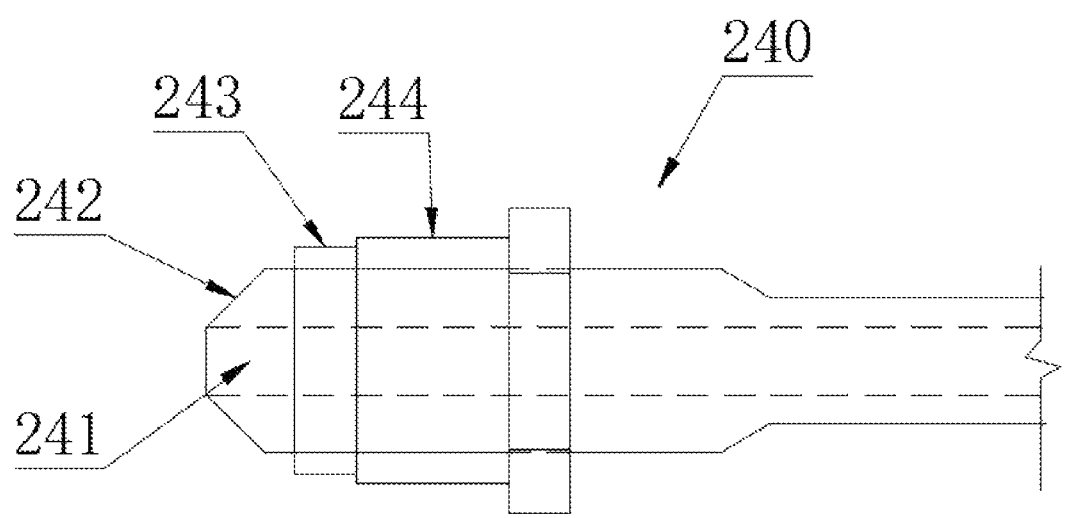
FIG. 9 is an implementation diagram of a water injection joint.

As shown in FIG. 2, in another preferred solution of the present disclosure, an upper seepage channel is provided in the upper specimen fixing head 210 and/or the pressure shaft 341. The upper seepage channel includes a first upper seepage fluid access opening located at a lower end of the pressure shaft 341 and a second upper seepage fluid access opening located on a side wall of the pressure shaft 341 or a side wall of the upper specimen fixing head 210. The lower specimen fixing head 220 is provided therein with a lower seepage channel. The lower seepage channel includes a first lower seepage fluid access opening located at the specimen fixing part of the lower specimen fixing head 220 and a second lower seepage fluid access opening located on a side wall of the lower specimen fixing head. The first upper seepage fluid access opening and the first lower seepage fluid access opening are respectively communicated with the two ends of the rock specimen 500 to form seepage access points and are communicated with a seepage fluid access opening of a seepage field module to form a seepage circuit. Typically, the first upper seepage fluid access opening and the first lower seepage fluid access opening are respectively communicated with the two ends of the rock specimen 500 through sealing joints 230. As shown in FIG. 8, the sealing joints 230 each generally include sealing joint body 231. Two ends of the sealing joint body 231 are respectively provided with sealing connection ends 232. The sealing connection ends 232 each are provided with end sealing ring 233. The sealing joint body 231 is typically made of a flexible or elastic material, preferably flexible rubber, to avoid damage in the event of a torsional difference. Typically, the second upper seepage fluid access opening and the second lower seepage fluid access opening are communicated with the seepage fluid access opening of the seepage field module through a water tube with water injection joint 240. As shown in FIG. 9, the water injection joint 240 generally includes water injection joint body 241. The water injection joint body 241 is sequentially provided with conical end 242, joint shoulder 243, and joint connecting sleeve 244 from front to back. The joint connecting sleeve 244 is sleeved outside the water injection joint body 241 and threaded to the second seepage fluid access opening.

The shear testing system of thermo-seepage-mechanical field and engineering disturbance coupling under deep and complex condition is communicated with the seepage fluid access opening of the seepage field module through the upper seepage channel and the lower seepage channel to form the seepage circuit, which facilitates the test of the rock specimen 500 under a seepage condition. The seepage field module mainly includes a water tank, a water pump, a water tube, an orifice plate, a regulating valve, and a flow meter. It can simulate a groundwater flow field to study the seepage performance of the rock specimen and acquire the seepage parameters of the rock specimen. Further, the seepage field can be coupled with a torsional shear to study the seepage—torsional shear performance of the rock specimen in a complex environment and acquire corresponding parameters of the rock specimen. The seepage field can be coupled with a triaxial confining pressure and a torsional shear to study the triaxial confining pressure—seepage—torsional shear performance of the rock specimen in a complex environment and acquire corresponding parameters of the rock specimen. The seepage field can be coupled with a triaxial confining pressure, an axial pressure, and a torsional shear to achieve a triaxial confining pressure—axial pressure—seepage—torsional shear coupled test. The design can provide experimental basis and data support for rock engineering exploration and design.

In a preferred implementation of the present disclosure, as shown in FIGS. 1, 2, and 3, the first mounting position of the device body 100 is corresponding to the upper specimen fixing head 210, and the power conversion assembly 300 is only provided at the first mounting position. The torque output component 310 is annular in shape. The power input component 320 is coaxial with the torque output component 310. The transmission mechanism 330 includes gear ring 331 located on a top surface of the torque output component 310 and surrounding the power input component 320, gear racks 332 located on the power input component 320 and distributed along the centerline of the motion trajectory of the power input component, and shaft gears 333 rotatably provided on the device body 100 and engaged with the gear ring 331 and the gear racks 332, respectively. The shaft gears 333 are generally rotatably connected to the device body 100 in a matched manner through a bearing, a shaft sleeve, or a shaft hole. The shear testing system features a simple and symmetrical structure, convenient processing and production, and high stability. When the power input component 320 is subjected to the axial pressure and moves downwards, the gear racks 332 drive the shaft gears 333 to rotate, causing the shaft gears 333 to drive the torque output component 310 to rotate, so as to apply a torque to the rock specimen 500. A lower end of the power input component 320 can pass through an inner hole of the torque output component 310. In order to facilitate the further downward movement of the power input component 320, an avoidance space corresponding to the power input component 320 is typically provided at an upper part of the upper specimen fixing head 210, as shown in FIG. 2.

In addition, the shaft gears 333 are engaged with the gear ring 331 and the gear racks 332 to achieve the transmission purpose of the transmission mechanism 330, and the engagement method has the following advantages. (1) Flexible transmission ratio. By designing the gear ratio of the shaft gears 333, the gear ring 331, and the gear racks 332, different transmission ratios can be achieved, making the transmission ratio easy to adjust and optimize. (2) High transmission accuracy. The tooth surfaces of the shaft gears 333, the gear ring 331, and the gear racks 332 are in continuous contact to effectively reduce run-out and vibration during motion, thereby achieving smooth motion transmission and ensuring accuracy. (3) Strong load-bearing capacity. Multiple tooth surfaces of the shaft gears 333 are in contact with the gear ring 331 and the gear racks 332 to effectively disperse the load, thereby increasing the load-bearing area and improving the load-bearing capacity. Such a structure can transmit a great power and torque, further facilitating the use of the shear testing system in conjunction with the axial pressure application device. (4) Easy processing and assembly. The tooth surface machining technology is mature and easy to acquire, and the assembly is relatively simple and direct, reducing the manufacturing difficulty and cost of components. (5) Compact structure. The shaft gears 333 are simultaneously engaged with the gear ring 331 and the gear racks 332, causing the power to be input and output at two ends within a short transmission distance, making the structure simple and compact.

Figure 4:
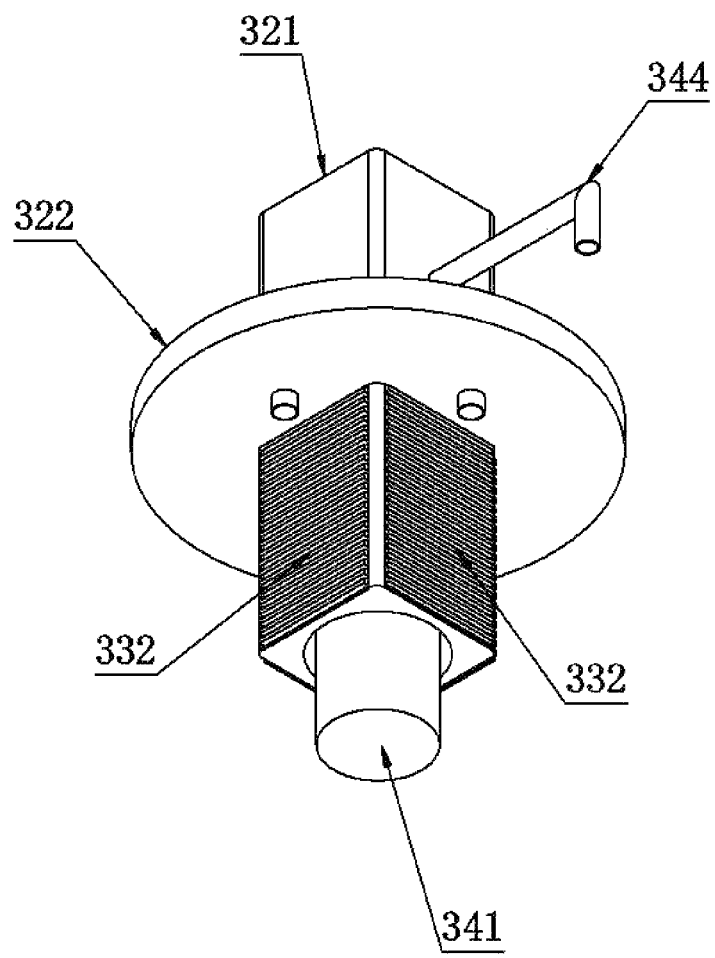
FIG. 4 is a three-dimensional structural diagram of a power input component.
Figure 5:
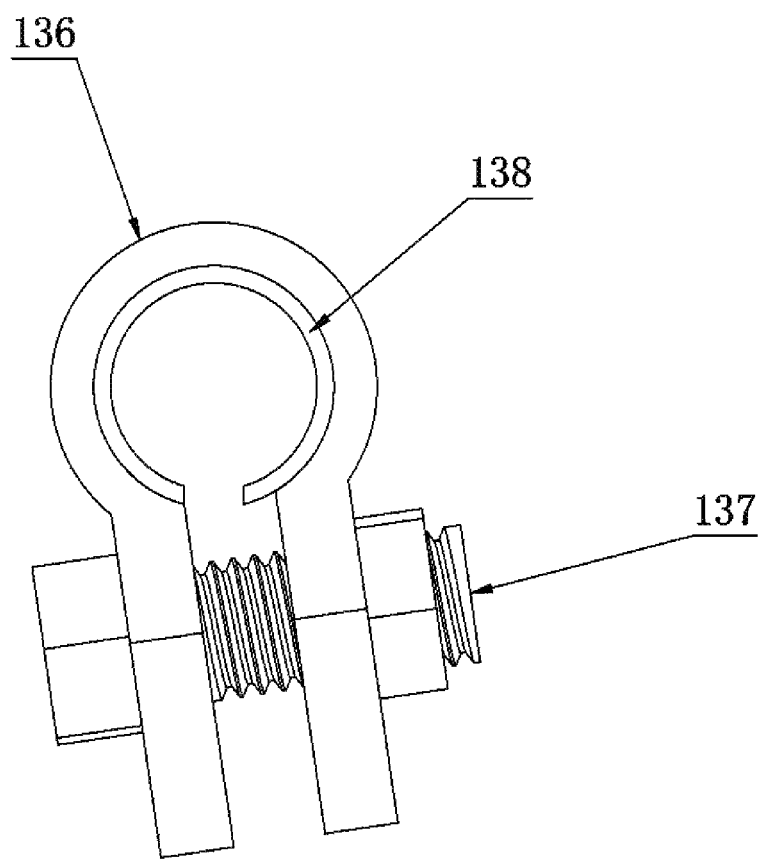
FIG. 5 is an implementation diagram of a ring clamp.

In order to facilitate the use of the power input component 320 in conjunction with the axial pressure application device, as shown in FIGS. 1, 2, and 4, the power input component 320 is provided with power input terminal 321 at an outer side of the device body 100. The power input terminal 321 is mainly configured to be abutted against or connected in a matched manner to an end of the pressure rod of the axial pressure application device. A surface of the power input terminal 321 forms the outer end surface of the power input component 320.

Preferably, as shown in FIGS. 1 and 2, in a preferred implementation of the power conversion assembly 300, the power input component 320 is provided with reset plate 322. The reset plate 322 is located at an upper side of the device cover 140, and reset spring 323 is provided between the reset plate 322 and the device cover 140. Through the reset plate 322 and the reset spring 323, after the axial pressure is removed, the power input component 320 of the power conversion assembly 300 can automatically reset to an initial position under an elastic force of the reset spring 323, such that the rock specimen 500 can be replaced with a new one for another test.

In order to ensure the accurate reset of the power conversion assembly 300, improve the stability of the power conversion assembly 300 and extend the service life of the reset mechanism, as shown in FIG. 1, in another preferred implementation of the power conversion assembly 300, on the basis of the above implementation, there are at least three reset springs 322 uniformly distributed around the power input component 320.

In order to further improve the stability and load-bearing capacity of the shear testing system, as shown in FIGS. 1, 2, 3, and 4, in another preferred implementation of the power conversion assembly 300, the power input component 320 is rectangular in shape, with the gear racks 332 on all four sides. Meanwhile, there are four shaft gears 333 that are respectively engaged with the gear racks 332 on the four sides of the power input component 320. The power conversion assembly 300 has a symmetrical structure and further increases the tooth surfaces in contact with the transmission mechanism, greatly improving the load-bearing capacity and transmission accuracy of the shear testing system.

In order to facilitate the mounting and setting of the shear testing system at a working position, as shown in FIGS. 1, 2, and 3, a bottom plate of the triaxial cell 600 forms the test bed 400, and the device body 100 is fixed to the test bed 400. Generally, the device base 120 of the device body 100 is fixedly connected to the test bed 400 through multiple base bolts. The triaxial cell 600 generally further includes a pressure chamber body mounted on the test bed 400 in a sealed manner through a sealing bolt. The heating element is provided in the triaxial pressure chamber 610 in various ways. In order to ensure the uniformity of the applied temperature field and improve the experimental effect, preferably, the heating element is provided in a spiral shape on a wall of the triaxial pressure chamber 610.

The present disclosure further provides a shear testing method of thermo-seepage-mechanical field and engineering disturbance coupling under deep and complex condition, which uses a shear testing system for rock testing. The shear testing system is the above-mentioned shear testing system of thermo-seepage-mechanical field and engineering disturbance coupling under deep and complex condition. The rock specimen 500 is tested by the shear testing method as follows.

Pre-preparation. Before a test begins, the rock specimen is first prepared and mounted. A rock processing procedure is needed to ensure the rock specimen 500 have standard test dimensions including diameter and length. The fixing joints, such as hexagonal joints, are attached to the ends of the rock specimen 500 through adhesive bonding. A through-hole for the pressure shaft 341 to penetrate can be reserved at the fixing joint at the end of the rock specimen 500 that requires an axial pressure to be applied. Sealing rings 520 are sleeved on the fixing joints, and the rock specimen 500 is wrapped with a heat shrink film. The heat shrink film is blown with hot air and compressed to form sealing film 510. Two ends of the sealing film 510 are respectively tightly sealed by the sealing rings 520 on the two fixing joints. Finally, the rock specimen 500 with its two ends attached to the fixing joints is fixed between the two specimen fixing heads of the shear testing system, such that the fixing joints are positioned and matched to the specimen fixing parts. At this point, the fixing operation of the rock specimen 500 is completed.

System debugging. The shear testing system with the rock specimen 500 fixed is mounted in an axial pressure application device (such as MTS) in a laboratory. The device base 120 is fixedly connected to the test bed 400. The pressure chamber 343 is communicated with the pressure shaft pressurization module in a cyclic manner, the triaxial pressure chamber 610 communicated with the confining pressure field module in a cyclic manner, and the heating element is electrically connected to the temperature field module. The pressure rod 710 of the axial pressure application device is just in contact with the outer end surface of the piston 342, and the axial pressure transducer shows data greater than zero. The amount of the pressure medium injected into the pressure chamber 343 is controlled to achieve an expected axial pressure on the rock specimen 500 during the test. The pressure medium transmits a pressure to all sides. The piston 342 tends to slide outward and transfers the pressure to the pressure rod 710. The pressure shaft 341 tends to move inward and directly transfers the axial pressure to the end of the rock specimen 500. At this point, the operation of pre-applying a constant axial pressure to the rock specimen 500 is completed.

Testing. The axial pressure of the pressure rod 710 serves as the power for the linear motion of the power input component 320 and the piston 342, and the linear motion of the power input component 320 is converted into the rotational motion of the torque output component 310 through the transmission mechanism 330. In addition, the torque output component 310 drives the specimen fixing head fixedly connected to the torque output component to rotate relative to the other specimen fixing head, thereby applying a torque to the rock specimen 500 fixed between the two specimen fixing heads. During this process, the piston 342 and the power input component 320 move axially synchronously. When the pressure generated by the pressure medium exceeds a set axial pressure, the pressure medium reaches a discharge threshold. The pressure medium is discharged to maintain a constant pressure transmitted to all sides, so as to maintain a constant axial pressure applied to the rock specimen 500. Alternatively, by injecting and/or discharging the pressure medium, the axial pressure applied to the rock specimen 500 meets an expected regular change for the test. Meanwhile, test oil is injected into the triaxial pressure chamber 610 through the confining pressure field module so as to apply a triaxial confining pressure to the rock specimen 500 fixed between the two specimen fixing heads. Besides, the heating element is controlled by the temperature field module to heat the test oil and the rock specimen 500 so as to apply a temperature field. And/or, the seepage fluid is circulated through the seepage field module to achieve uniaxial seepage on the rock specimen 500. In this way, the rock specimen 500 is subjected to a triaxial confining pressure—temperature—axial pressure—torsional shear coupled test, a triaxial confining pressure—axial pressure—seepage—torsional shear coupled test, and a triaxial confining pressure—temperature—axial pressure—seepage—torsional shear coupled test. Finally, the deformation and failure of the rock specimen 500 during the test are measured, and stress-strain, axial pressure, torsion angle, torque, triaxial pressure, temperature, seepage, and other data of the rock specimen 500 are acquired for data analysis.

Figure 11:
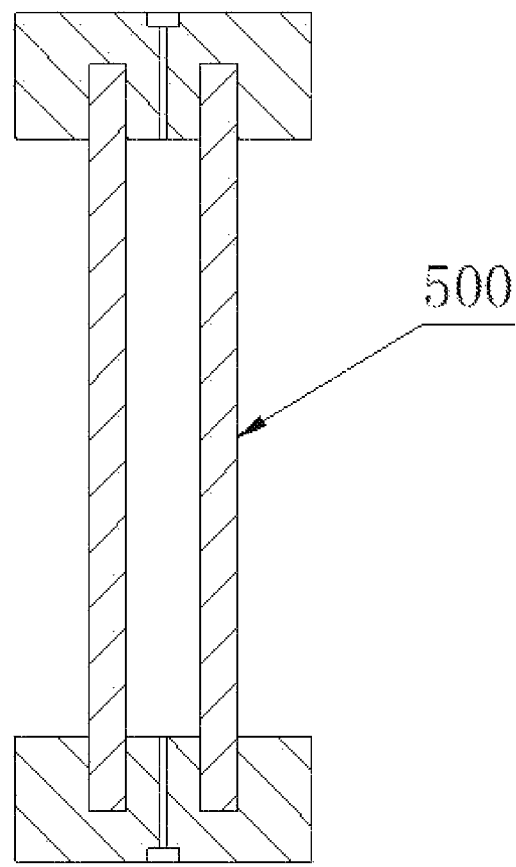
FIG. 11 is a structural diagram of a hollow cylindrical rock specimen.
Figure 12:
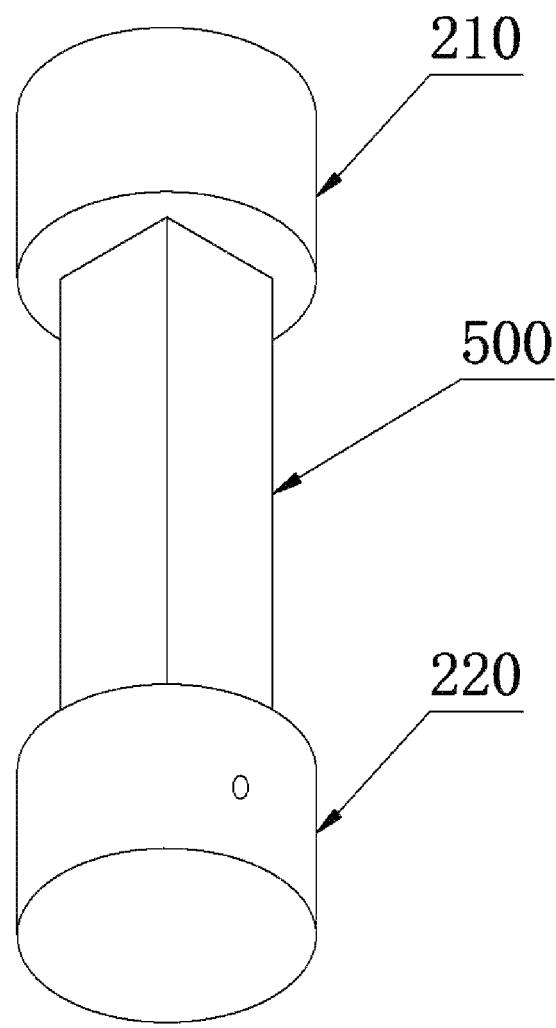
FIG. 12 is a structural diagram of a solid square-columnar rock specimen.
Figure 13:
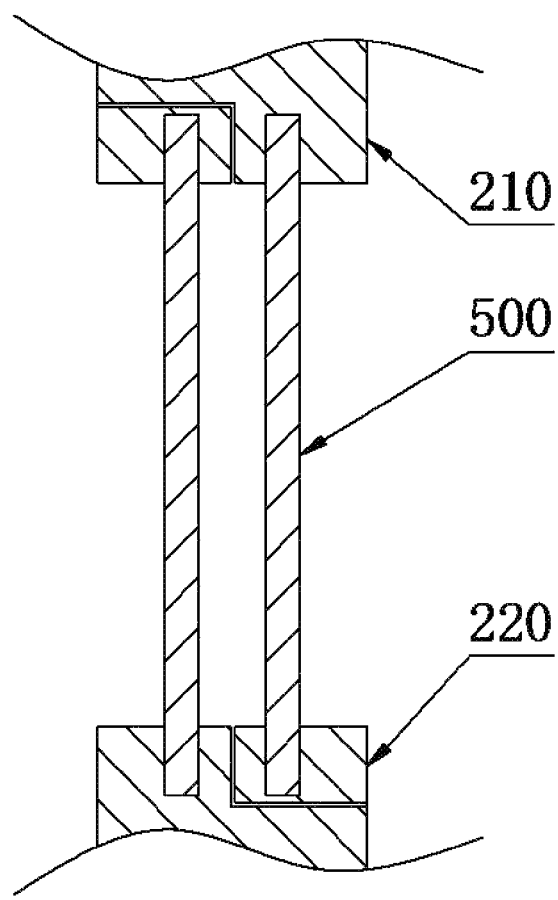
FIG. 13 is a structural diagram of a hollow square-columnar rock specimen.

In the above test, it is necessary to follow relevant operation rules of rock testing to complete mounting, sealing, filling (the test oil), and heating operations of the triaxial cell 600. For instruments that acquires parameters such as stress-strain, triaxial pressure, axial pressure, torsion angle, and/or torque, their positions and arrangement methods are available in the prior art. Typically, the stress-strain or torsion angle acquisition instrument can be mounted between the specimen fixing head and the rock specimen 500. For the convenience of detecting the torque applied for the test, torque transducer 820 corresponding to the torque output component 310 or the specimen fixing head connected to the torque output component 310 can typically be provided. For hollow rock specimen 500, typically, the first upper seepage fluid access opening and the first lower seepage fluid access opening are communicated with the inner cavity of the rock specimen 500, as shown in FIG. 13. If there are fixing joints adhered, flow passages are typically provided inside the fixing joints to communicate the first upper seepage fluid access opening and the first lower seepage fluid access opening with the inner cavity of the rock specimen 500 respectively, as shown in FIG. 11. The design achieves the seepage of the rock specimen 500, and the seepage fluid in the inner cavity of the rock specimen can partially or completely offset the confining pressure on the rock specimen 500.

Figure 6:
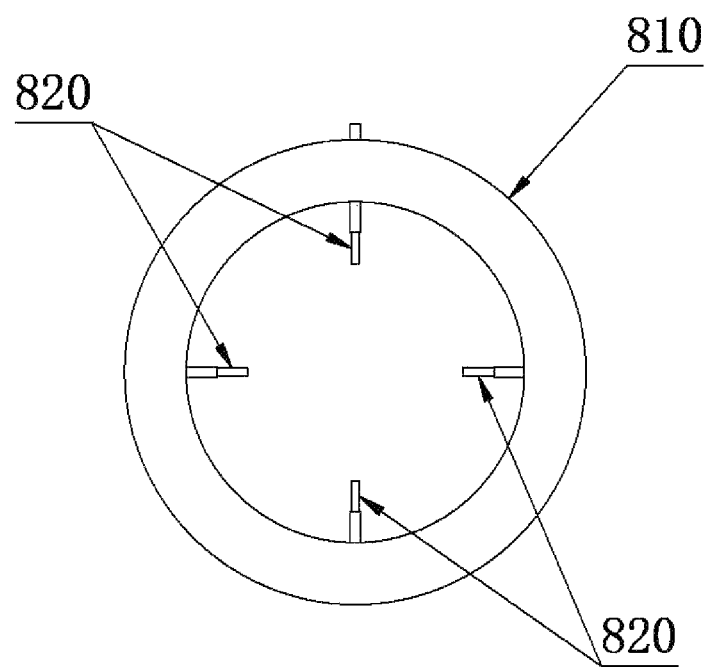
FIG. 6 is a mounting diagram of a torque transducer.

For example, as shown in FIG. 6, in a preferred implementation of the torque transducer 820, torque transducer mounting seat 810 with an annular structure is provided, which is coaxial with the torque output component 310 or the specimen fixing head connected to the torque output component 310. The torque transducer 820 is located on the torque transducer mounting seat 810. A probe of the torque transducer 820 is in contact with the torque output component 310 or the specimen fixing head. In order to improve the accuracy of torque detection, preferably, multiple uniformly distributed torque transducers 820 are arranged on the torque transducer mounting seat 810.

Figure 7:
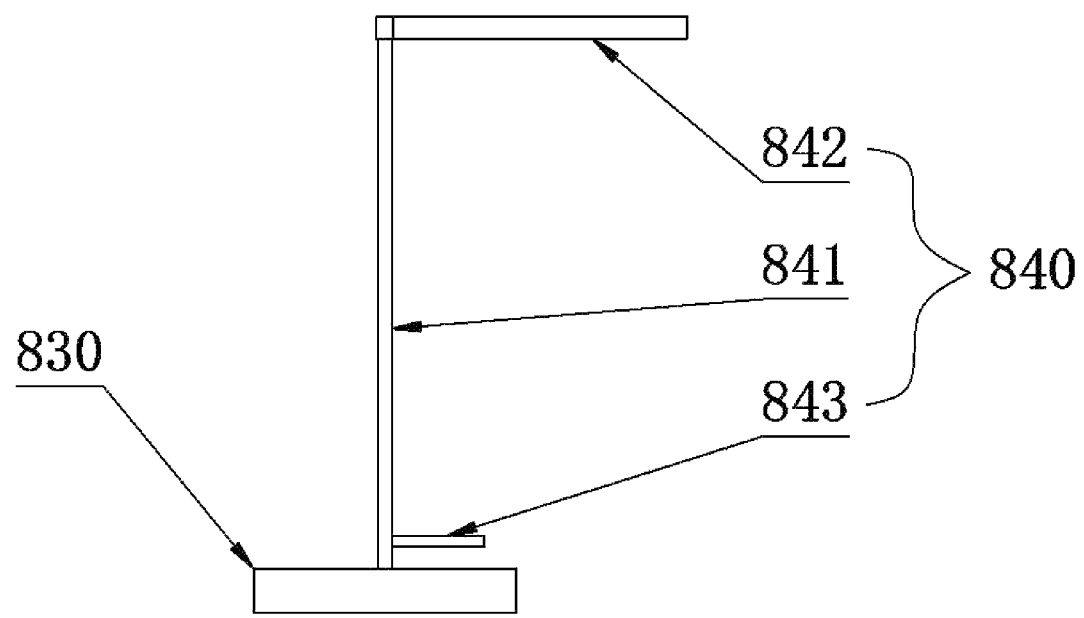
FIG. 7 is a mounting diagram of an angle transducer.

For example, as shown in FIG. 7, in a preferred implementation of the angle transducer 840, angle transducer mounting seat 830 is provided in the rock specimen 500 of a hollow structure. The angle transducer 840 is located on the angle transducer mounting seat 830. The angle transducer 840 generally includes angle transducer body 841 vertically provided in a center of the angle transducer mounting seat 830, angle transducer upper-end pointer 842 provided at an upper end of the angle transducer body 841, and angle transducer lower-end pointer 843 provided at a lower end of the angle transducer upper-end pointer 842.

What is claimed is:

1. A deep underground multi-field and complex stress-coupled shear testing system, comprising a device body and a specimen fixing mechanism, wherein
    the device body is provided therein with a working chamber;
    the specimen fixing mechanism comprises two specimen fixing heads that are arranged opposite in the working chamber; and corresponding positions of the two specimen fixing heads are respectively provided with specimen fixing parts;
    the shear testing system further comprises a power conversion assembly and a triaxial cell;
    the device body comprises a device base, support rods provided on the device base, and a device cover provided on top ends of the support rods;
    the working chamber is a space between the device base and the device cover;
    the device body is provided with a first mounting position and a second mounting position that are respectively corresponding to the two specimen fixing heads; the two specimen fixing heads comprise an upper specimen fixing head and a lower specimen fixing head that are arranged above and below; and the lower specimen fixing head is fixedly connected to the device base;
    the first mounting position of the device body is corresponding to the upper specimen fixing head, and only the first mounting position is provided with the power conversion assembly; and
    the power conversion assembly comprises a torque output component, a power input component, a transmission mechanism, and an axial pressure mechanism;
    the torque output component is annular in shape; and the torque output component is rotatably provided on the device body, fixedly connected to the corresponding upper specimen fixing head, and able to drive the upper specimen fixing head to rotate relative to the lower specimen fixing head;
    the power input component is coaxial with the torque output component and linearly movable;
    the transmission mechanism is in transmission connection with the torque output component and the power input component, and is able to convert a linear motion of the power input component into a rotational motion of the torque output component;
    the transmission mechanism comprises a gear ring located on a top surface of the torque output component and surrounding the power input component, gear racks located on the power input component and distributed along a centerline of a motion trajectory of the power input component, and shaft gears rotatably provided on the device body and engaged with the gear ring and the gear racks, respectively;
    the axial pressure mechanism comprises a pressure shaft slidably provided inside the power input component; an inner end of the pressure shaft sequentially passes through an inner end of the power input component, the torque output component, and the upper specimen fixing head connected to the torque output component, and extends to the specimen fixing part of the upper specimen fixing head; and an outer end of the pressure shaft is provided with a sliding groove;
    the axial pressure mechanism further comprises a piston that is slidably provided in the sliding groove of the pressure shaft and forms a pressure chamber with the sliding groove; the pressure chamber is filled with a pressure medium; and the pressure medium is configured to generate a pressure to make an outer end surface of the piston flush with an outer end surface of the power input component; and
    an inner chamber of the triaxial cell forms a triaxial pressure chamber; the triaxial cell is provided with a pressure rod through-hole for a pressure rod to penetrate into the triaxial pressure chamber; the triaxial pressure chamber is provided therein with a heating element; the device body is located in the triaxial pressure chamber; and there is at least one power input component corresponding to the pressure rod through-hole.

2. The deep underground multi-field and complex stress-coupled shear testing system according to claim 1, wherein the support rods are telescopic support rods with an adjustable length; and there are at least three support rods distributed in a ring array.

3. The deep underground multi-field and complex stress-coupled shear testing system according to claim 2, wherein the axial pressure mechanism further comprises a pressure medium inlet tube and a pressure medium outlet tube that are communicated with the pressure chamber, as well as a clamp projection provided in the sliding groove of the pressure shaft for limiting the piston.

4. The deep underground multi-field and complex stress-coupled shear testing system according to claim 3, wherein the shear testing system further comprises a pressure shaft pressurization module, a confining pressure field module, and a temperature field module;
the pressure shaft pressurization module comprises a pressure medium outlet connected to the pressure medium inlet tube and a pressure medium inlet connected to the pressure medium outlet tube;
the confining pressure field module comprises a confining pressure medium outlet communicated with a pressurization port of the triaxial cell and a confining pressure medium inlet communicated with a pressure relief port of the triaxial cell; and
the temperature field module comprises a temperature field controller, a temperature field transducer, and a power supply; the temperature field transducer is provided in the triaxial pressure chamber, and the heating element, the temperature field transducer, and the power supply are all electrically connected to the temperature field controller.

5. The deep underground multi-field and complex stress-coupled shear testing system according to claim 4, wherein the power input component is rectangular in shape, with the gear racks on all four sides; and
there are four shaft gears respectively engaged with the gear racks on the four sides of the power input component.

6. The deep underground multi-field and complex stress-coupled shear testing system according to claim 2, wherein the power input component is rectangular in shape, with the gear racks on all four sides; and
there are four shaft gears respectively engaged with the gear racks on the four sides of the power input component.

7. The deep underground multi-field and complex stress-coupled shear testing system according to claim 3, wherein the power input component is rectangular in shape, with the gear racks on all four sides; and
there are four shaft gears respectively engaged with the gear racks on the four sides of the power input component.

8. The deep underground multi-field and complex stress-coupled shear testing system according to claim 1, wherein an upper seepage channel is provided in the upper specimen fixing head and/or the pressure shaft; and the upper seepage channel comprises a first upper seepage fluid access opening located at a lower end of the pressure shaft and a second upper seepage fluid access opening located on a side wall of the pressure shaft or a side wall of the upper specimen fixing head; and
the lower specimen fixing head is provided therein with a lower seepage channel; and the lower seepage channel comprises a first lower seepage fluid access opening located at the specimen fixing part of the lower specimen fixing head and a second lower seepage fluid access opening located on a side wall of the lower specimen fixing head.

9. The deep underground multi-field and complex stress-coupled shear testing system according to claim 8, wherein the power input component is rectangular in shape, with the gear racks on all four sides; and
there are four shaft gears respectively engaged with the gear racks on the four sides of the power input component.

10. The deep underground multi-field and complex stress-coupled shear testing system according to claim 1, wherein the power input component is provided with a power input terminal at an outer side of the device body; and a surface of the power input terminal forms the outer end surface of the power input component; and
the power input component is provided with a reset plate; the reset plate is located at an upper side of the device cover; and a reset spring is provided between the reset plate and the device cover.

11. The deep underground multi-field and complex stress-coupled shear testing system according to claim 10, wherein the power input component is rectangular in shape, with the gear racks on all four sides; and
there are four shaft gears respectively engaged with the gear racks on the four sides of the power input component.

12. The deep underground multi-field and complex stress-coupled shear testing system according to claim 1, wherein the power input component is rectangular in shape, with the gear racks on all four sides; and
there are four shaft gears respectively engaged with the gear racks on the four sides of the power input component.

13. The deep underground multi-field and complex stress-coupled shear testing system according to claim 12, wherein a bottom plate of the triaxial cell forms a test bed; and
the device body is fixed to the test bed.

14. A deep underground multi-field and complex stress-coupled shear testing method, for rock testing by a shear testing system, wherein the shear testing system is the deep underground multi-field and complex stress-coupled shear testing system according to claim 1, and the shear testing method comprises the following steps:
step 1: preparing a rock specimen; wrapping the rock specimen with a sealing film that comprises two ends sealed by sealing rings, respectively; and fixing the rock specimen between the upper specimen fixing head and the lower specimen fixing head of the shear testing system;
step 2: mounting the shear testing system with the fixed rock specimen on an axial pressure application device; communicating the pressure chamber with a pressure shaft pressurization module in a cyclic manner, communicating the triaxial pressure chamber with a confining pressure field module in a cyclic manner, and electrically connecting the heating element to a temperature field module; making the pressure rod of the axial pressure application device just in contact with the outer end surface of the piston; and controlling an amount of the pressure medium injected into the pressure chamber to apply a constant axial pressure to the rock specimen;
step 3: driving, by the axial pressure application device, the power input component and the piston to move linearly; converting, by the transmission mechanism, the linear motion of the power input component into a rotational motion of the torque output component; driving, by the torque output component, the upper specimen fixing head fixedly connected to the torque output component to rotate relative to the lower specimen fixing head, thereby applying a torque to the rock specimen; causing the piston and the power input component to move axially synchronously; and controlling, by the pressure shaft pressurization module, the amount of the pressure medium injected into the pressure chamber, so as to maintain a constant axial pressure applied to the rock specimen or to ensure that the axial pressure applied to the rock specimen changes as expected for testing; and injecting, by the confining pressure field module, test oil into the triaxial pressure chamber to apply a triaxial confining pressure to the rock specimen; and controlling, by the temperature field module, the heating element to heat the test oil and the rock specimen; and step 4: subjecting the rock specimen to a triaxial confining pressure—temperature—axial pressure—torsional shear coupled test; measuring a deformation and failure of the rock specimen during the test; and acquiring data for analysis.

15. The deep underground multi-field and complex stress-coupled shear testing method according to claim 14, wherein in the deep underground multi-field and complex stress-coupled shear testing system, the support rods are telescopic support rods with an adjustable length; and there are at least three support rods distributed in a ring array.

16. The deep underground multi-field and complex stress-coupled shear testing method according to claim 15, wherein in the deep underground multi-field and complex stress-coupled shear testing system, the axial pressure mechanism further comprises a pressure medium inlet tube and a pressure medium outlet tube that are communicated with the pressure chamber, as well as a clamp projection provided in the sliding groove of the pressure shaft for limiting the piston.

17. The deep underground multi-field and complex stress-coupled shear testing method according to claim 16, wherein the deep underground multi-field and complex stress-coupled shear testing system further comprises the pressure shaft pressurization module, the confining pressure field module, and the temperature field module;

the pressure shaft pressurization module comprises a pressure medium outlet connected to the pressure medium inlet tube and a pressure medium inlet connected to the pressure medium outlet tube;

the confining pressure field module comprises a confining pressure medium outlet communicated with a pressurization port of the triaxial cell and a confining pressure medium inlet communicated with a pressure relief port of the triaxial cell; and the temperature field module comprises a temperature field controller, a temperature field transducer, and a power supply; the temperature field transducer is provided in the triaxial pressure chamber, and the heating element, the temperature field transducer, and the power supply are all electrically connected to the temperature field controller.

18. The deep underground multi-field and complex stress-coupled shear testing method according to claim 14, wherein in the deep underground multi-field and complex stress-coupled shear testing system, an upper seepage channel is provided in the upper specimen fixing head and/or the pressure shaft; and the upper seepage channel comprises a first upper seepage fluid access opening located at a lower end of the pressure shaft and a second upper seepage fluid access opening located on a side wall of the pressure shaft or a side wall of the upper specimen fixing head; and the lower specimen fixing head is provided therein with a lower seepage channel; and the lower seepage channel comprises a first lower seepage fluid access opening located at the specimen fixing part of the lower specimen fixing head and a second lower seepage fluid access opening located on a side wall of the lower specimen fixing head.

19. The deep underground multi-field and complex stress-coupled shear testing method according to claim 14, wherein in the deep underground multi-field and complex stress-coupled shear testing system, the power input component is provided with a power input terminal at an outer side of the device body; and a surface of the power input terminal forms the outer end surface of the power input component; and the power input component is provided with a reset plate; the reset plate is located at an upper side of the device cover; and a reset spring is provided between the reset plate and the device cover.

20. The deep underground multi-field and complex stress-coupled shear testing method according to claim 14, wherein in the deep underground multi-field and complex stress-coupled shear testing system, the power input component is rectangular in shape, with the gear racks on all four sides; and there are four shaft gears respectively engaged with the gear racks on the four sides of the power input component.

* * * * *